/

US009717835B2

(12) United States Patent
Borenstein et al.

(10) Patent No.: US 9,717,835 B2
(45) Date of Patent: Aug. 1, 2017

(54) BLOOD OXYGENATOR (71) Applicant: The Charles Stark Draper Laboratory, Inc., Cambridge, MA (US)

(72) Inventors: Jeffrey T. Borenstein, Newton, MA (US); Ernest Kim, Cambridge, MA (US); Joseph L. Charest, Cambridge, MA (US); Alla Epshteyn, Tampa, FL (US); Abigail Spencer, Boston, MA (US); James Truslow, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 14/694,628

(22) Filed: Apr. 23, 2015

(65) Prior Publication Data
US 2015/0306296 A1    Oct. 29, 2015

Related U.S. Application Data

(60) Provisional application No. 61/983,314, filed on Apr. 23, 2014.

(51) Int. Cl.
*A61M 1/00* (2006.01)
*A61M 1/32* (2006.01)
(Continued)

(52) U.S. Cl.
CPC ............ *A61M 1/32* (2013.01); *A61M 1/1698* (2013.01); *B32B 38/18* (2013.01);
(Continued)

(58) Field of Classification Search
CPC ....... A61M 1/32; A61M 1/1698; B32B 37/06; B32B 37/12; B32B 37/182; B32B 37/1841; B32B 38/1808; B32B 38/1841
(Continued)

(56) References Cited

U.S. PATENT DOCUMENTS 2,876,769 A    3/1959    Cordova
2,985,588 A    5/1961    Binning et al.
(Continued)

FOREIGN PATENT DOCUMENTS

DE    102008045621 A1    3/2010
EP            041692    12/1981
(Continued)

OTHER PUBLICATIONS

Chinese Search Report dated Oct. 26, 2015 for Chinese Patent Application No. 2012800595919.
(Continued)

*Primary Examiner* — Philip R Wiest
(74) *Attorney, Agent, or Firm* — McDermott Will & Emery LLP (57) ABSTRACT

The present disclosure describes a blood oxygenator that includes a checkerboard layout of fluid (e.g., blood) and gas (e.g., oxygen) channels. When viewed as a cross-section through each of the channels of the oxygenator, the checkerboard configuration includes alternating gas and fluid channels in both the x-axis (e.g., in-plane) and in the y-axis (e.g., out-of-plane) directions. The oxygenator described herein reduces manufacturing complexity by using first, second, and third polymer layers that include asymmetrical channel designs. The channel designs include "open" gas channels, which are exposed to the ambient atmosphere. The oxygenator is placed within a pressure vessel to drive gas into each of the open gas channels, which in some implementations, negates the need for a gas manifold.

21 Claims, 7 Drawing Sheets

(51) Int. Cl.
| | |
|---|---|
| *B32B 38/18* | (2006.01) |
| *A61M 1/16* | (2006.01) |
| *B32B 37/06* | (2006.01) |
| *B32B 37/12* | (2006.01) |
| *B32B 37/18* | (2006.01) |
| *B32B 38/00* | (2006.01) |
| *B29C 65/08* | (2006.01) |
| *B29C 65/16* | (2006.01) |
| *B29C 65/48* | (2006.01) |
| *B29C 65/00* | (2006.01) |
| *B29L 31/00* | (2006.01) |
| *B29C 65/06* | (2006.01) |

(52) U.S. Cl.
CPC . *B32B 38/1808* (2013.01); *A61M 2205/0244* (2013.01); *B29C 65/06* (2013.01); *B29C 65/08* (2013.01); *B29C 65/16* (2013.01); *B29C 65/483* (2013.01); *B29C 65/4815* (2013.01); *B29C 66/1122* (2013.01); *B29C 66/543* (2013.01); *B29L 2031/756* (2013.01); *B32B 37/06* (2013.01); *B32B 37/12* (2013.01); *B32B 37/182* (2013.01); *B32B 38/0008* (2013.01); *B32B 38/1841* (2013.01); *B32B 2307/724* (2013.01); *B32B 2535/00* (2013.01)

(58) Field of Classification Search
USPC ............................. 604/4.01–6.12; 422/44–48
See application file for complete search history.

(56) References Cited

U.S. PATENT DOCUMENTS

| | | | |
|---|---|---|---|
| 3,489,647 A | 1/1970 | Kolobow | |
| 3,738,813 A | 6/1973 | Esmond | |
| 3,834,544 A | 9/1974 | Tyson et al. | |
| 3,847,211 A * | 11/1974 | Fischel | B01D 53/22 165/166 |
| 4,075,091 A | 2/1978 | Bellhouse | |
| 4,415,447 A | 11/1983 | Foucras et al. | |
| 4,583,969 A | 4/1986 | Mortensen | |
| 4,620,965 A | 11/1986 | Fukusawa et al. | |
| 4,756,835 A | 7/1988 | Wilson | |
| 4,997,565 A | 3/1991 | Niesen | |
| 5,120,445 A | 6/1992 | Colman | |
| 5,192,320 A | 3/1993 | Anazawa et al. | |
| 5,207,639 A | 5/1993 | Cooper | |
| 5,254,259 A | 10/1993 | Bellhouse et al. | |
| 5,338,770 A | 8/1994 | Winters et al. | |
| 5,411,650 A | 5/1995 | Frank | |
| 6,241,945 B1 | 6/2001 | Owen | |
| 6,416,666 B1 | 7/2002 | Salyer et al. | |
| 6,514,412 B1 | 2/2003 | Insley et al. | |
| 6,602,468 B2 | 8/2003 | Patterson et al. | |
| 7,569,144 B2 | 8/2009 | De Biran et al. | |
| 7,713,544 B2 | 5/2010 | Chaikof et al. | |
| 7,759,113 B2 | 7/2010 | Vacanti et al. | |
| 7,955,504 B1 * | 6/2011 | Jovanovic | B01D 61/18 210/321.71 |
| 8,128,822 B2 | 3/2012 | Browning et al. | |
| 8,137,554 B2 | 3/2012 | Jovanovic et al. | |
| 8,266,791 B2 | 9/2012 | Borenstein et al. | |
| 8,647,410 B2 | 2/2014 | Borenstein et al. | |
| 8,728,214 B2 | 5/2014 | Maurer | |
| 9,180,239 B2 | 11/2015 | Borenstein et al. | |
| 2002/0182241 A1 | 12/2002 | Borenstein et al. | |
| 2003/0064003 A1 | 4/2003 | Takehisa et al. | |
| 2003/0121841 A1 | 7/2003 | Harttig et al. | |
| 2003/0175149 A1 | 9/2003 | Searles et al. | |
| 2005/0202557 A1 | 9/2005 | Borenstein et al. | |
| 2006/0136182 A1 | 6/2006 | Vacanti et al. | |
| 2006/0173394 A1 | 8/2006 | Stroock et al. | |
| 2007/0119771 A1 | 5/2007 | Schukar et al. | |
| 2008/0093298 A1 | 4/2008 | Browning et al. | |
| 2009/0081079 A1 | 3/2009 | Johns | |
| 2009/0098017 A1 * | 4/2009 | Celik-Butler | A61M 1/16 422/48 |
| 2009/0234332 A1 | 9/2009 | Borenstein et al. | |
| 2010/0098742 A1 | 4/2010 | Vacanti et al. | |
| 2010/0118642 A1 | 5/2010 | Ho et al. | |
| 2010/0267136 A1 | 10/2010 | Vacanti et al. | |
| 2011/0158847 A1 * | 6/2011 | Charest | A61M 1/14 422/45 |
| 2011/0186165 A1 | 8/2011 | Borenstein et al. | |
| 2011/0226686 A1 * | 9/2011 | Maurer | A61M 1/1698 210/206 |
| 2011/0290113 A1 | 12/2011 | Borenstein et al. | |
| 2012/0182609 A1 | 7/2012 | Borenstein et al. | |
| 2013/0144266 A1 | 6/2013 | Borenstein et al. | |
| 2013/0197420 A1 | 8/2013 | Fissell et al. | |
| 2014/0150662 A1 | 6/2014 | Vandermeulen et al. | |
| 2014/0255253 A1 | 9/2014 | Fusch et al. | |

FOREIGN PATENT DOCUMENTS

| | | |
|---|---|---|
| GB | 1408562 A | 10/1975 |
| JP | S62-064372 A | 3/1987 |
| JP | 2003093853 A | 4/2003 |
| WO | 02076529 A1 | 10/2002 |
| WO | 2006042079 A1 | 4/2006 |
| WO | 2010025926 A1 | 3/2010 |
| WO | 2011150216 A1 | 12/2011 |

OTHER PUBLICATIONS

Decision of Rejection issued Jan. 6, 2016 in Japanese Patent Application No. 2013-512244.
First Office Action dated Nov. 4, 2015 for Chinese Patent Application No. 2012800595919 (with English Translation).
King Saud University "Reverse Osmosis" pp. 409-452, Sep. 30, 2010, http://faculty.ksu.edu.sa/Almutaz/Documents/ChE-413/Reverse%20Osmosis.pdf.
US Office Action on U.S. Appl. No. 14/177,799 DTD Oct. 28, 2015.
U.S. Appl. No. 13/705,795, filed Dec. 5, 2012.
U.S. Appl. No. 12/981,0903, filed Dec. 30, 2010.
U.S. Appl. No. 13/116,219, filed May 26, 2011.
U.S. Appl. No. 14/177,799, filed Feb. 11, 2014.
International Search Report and Written Opinion dated Jul. 17, 2015 in PCT Application No. PCT/US2015/027321.
U.S. Notice of Allowance in U.S. Appl. No. 13/705,795 DTD Aug. 19, 2015.
U.S. Notice of Allowance in U.S. Appl. No. 12/981,903 DTD May 19, 2015.
U.S. Notice of Allowance on U.S. Appl. No. 13/705,795 DTD Oct. 7, 2015.
Office Action dated Feb. 10, 2017 in Australian Patent Application No. 2012347922.
Office Action dated Sep. 29, 2014 in Australian Patent Application No. 2010339409.
Office Action dated Nov. 4, 2014 in Australian Patent Application No. 2011258203.
Burgess et al., Towards Microfabricated Biohybrid Artificial Lung Modules for Chronic Respiratory Support, Biomedical Microdevices, vol. 11, No. 12, pp. 117-127 (2008).
Borenstein et al., Microfabrication Technology for Vascularized Tissue Engineering, Biomedical Microdevices, vol. 4, No. 3, pp. 167-175 (2002).
Office Action dated Aug. 12, 2016 in Canadian Patent Application No. 2,786,008.
Office Action dated Jun. 3, 2016 in Chinese Patent Application No. 201280059591.9.
Office Action dated Jul. 17, 2014 in Chinese Patent Application No. 201180036712.3.
Office Action dated Dec. 2, 2016 in Chinese Patent Application No. 201280059591.9.
Office Action dated Jan. 5, 2017 in European Patent Application No. 12799501.7.

(56) References Cited

OTHER PUBLICATIONS

Office Action dated Aug. 31, 2016 in European Patent Application No. 11725262.7.
Office Action dated Mar. 26, 2015 in Japanese Patent Application No. 2013-512244.
Office Action dated Oct. 13, 2016 in Japanese Patent Application No. 2014-546025.
Office Action dated Dec. 4, 2014 in Japanese Patent Application No. 2012-547304.
Kuo, Alex C. M., Poly (dimethylsiloxane), Polymer data handbook, 1999 Oxford University Press, Inc.
Leclerc et al., Cell Culture in 3-Dimensional Microfluidic Structure of Pdms (polydimethylsiloxane), Biomedical Microdevices, vol. 5, vol. 2, pp. 109-114 (2003).
International Search Report and Written Opinion issued Mar. 12, 2013 in PCT Application No. PCT/US2012/067971.
International Search Report and Written Opinion issued May 2, 2011 in PCT Application No. PCT/US2010/062537.
International Search Report and Written Opinion issued Aug. 26, 2011 in PCT Application No. PCT/US2011/038148.
Stroock, et al, Chaotic Mixer for Microchannels, Science, vol. 295, Jan. 25, 2002, pp. 647-651.
U.S. Notice of Allowance dated Feb. 2, 2015 in U.S. Appl. No. 12/981,903.
U.S. Notice of Allowance dated Feb. 26, 2016 in U.S. Appl. No. 14/177,799.
U.S. Notice of Allowance dated Jun. 14, 2013 in U.S. Appl. No. 13/116,219.
U.S. Notice of Allowance dated Sep. 10, 2015 in U.S. Appl. No. 13/705,795.
U.S. Notice of Allowance dated Oct. 4, 2013 in U.S. Appl. No. 13/116,219.
U.S. Office Action dated Feb. 22, 2013 in U.S. Appl. No. 12/981,901.
U.S. Office Action dated Aug. 30, 2012 in U.S. Appl. No. 12/981,903.
U.S. Office Action dated Sep. 11, 2013 in U.S. Appl. No. 12/981,903.
U.S. Office Action dated Mar. 13, 2015 in U.S. Appl. No. 13/705,795.
U.S. Office Action dated May 16, 2014 in U.S. Appl. No. 13/705,795.
U.S. Office Action dated Oct. 22, 2014 in U.S. Appl. No. 13/705,795.
Wu et al., Construction of Microfluidic Chips Using Polydimethylsiloxane for Adhesive Bonding, Lab on a Chip, vol. 5, pp. 1393-1398 (2005).
Yasuda, H. Units of Gas Permeability Constants, Journal of Applied Polymer Science, 1975, vol. 19, pp. 2529-2536.

\* cited by examiner

BLOOD OXYGENATOR

CROSS-REFERENCE TO RELATED PATENT APPLICATIONS

This application claims priority to U.S. Provisional Patent Application No. 61/983,314 filed on Apr. 23, 2014 and titled "Blood Oxygenator," which is herein incorporated by reference in its entirety.

BACKGROUND OF THE DISCLOSURE

Oxygenators can be used as lung assist devices to supplement the oxygenation performed by damaged or diseased lungs. Standard configurations for blood oxygenators are based on hollow fiber networks. Hollow fiber networks can require high levels of anticoagulants that tend to cause damage to the blood flowing through the oxygenator. The hollow fiber oxygenators can also have relatively long blood flow paths, residence times, and large blood prime volumes.

SUMMARY OF THE DISCLOSURE

According to one aspect of the disclosure, an oxygenator includes a first polymer layer that defines a first plurality of gas channels and a first plurality of fluid channels, a second polymer layer that defines a second plurality of gas channels and a second plurality of fluid channels. Each of the second plurality of gas channels overlap one of the first plurality of fluid channels. Each of the second plurality of fluid channels overlap one of the first plurality of gas channels. The oxygenator also includes a third polymer layer that defines a third plurality of gas channels and a third plurality of fluid channels. Each of the third plurality of gas channels overlap one of the second plurality of fluid channels and each of the third plurality of fluid channels overlap one of the second plurality of gas channels. The second polymer layer also defines a plurality of gas vias. Each of the plurality of gas vias couple one of the first plurality of gas channels to one of the third plurality of gas channels.

In some implementations, the first polymer layer defines a second plurality of gas vias and the third polymer layer defines a third plurality of gas vias. The first plurality of gas channels and the third plurality of gas channels define a first gas flow network, and the second plurality of gas channels define a second gas flow network.

In some implementations, the oxygenator includes a pressure vessel that houses the first, second, and third polymer layers. An inlet to the first, second, and third plurality of gas channels is open to an ambient environment within the pressure vessel.

In some implementations, the first plurality of gas channels and the first plurality of fluid channels are configured in an asymmetrical channel layout. The second plurality of gas channels and the second plurality of fluid channels are also configured in the asymmetrical channel layout. In some implementations, the second and third polymer layers are each a copy of the first polymer layer. In some implementations, the second polymer layer is rotated 180 degrees with respect to the first and third polymer layers.

In some implementations, each of the channels of the first, second, and third plurality of gas channels comprise a dead end. In some implementations, the first, second, and third polymer layers each comprise Poly(DiMethylSiloxane). In some implementations, the first, second, and third polymer layers each have a gas permeance greater than about $1 \times 10^{-6}$ mL/s/cm²/cm Hg. In some implementations, a depth of the first, second, and third plurality of fluid channels is between about 40 μm and about 250 μm. In some implementations, each of the plurality of gas vias is positioned between two of the plurality of fluid channels of the second polymer layer. In some implementations, each of the plurality of gas vias is aligned with a longitudinal axis of one of the plurality of fluid channels in the second polymer layer.

In some implementations, each of the second plurality of fluid channels are substantially vertically aligned with one of the first plurality of gas channels, each of the third plurality of gas channels are substantially vertically aligned with one of the second plurality of fluid channels, and each of the third plurality of fluid channels are substantially vertically aligned with one of the second plurality of gas channels. In some implementations, the gas and fluid channels of the first, second, and third polymer layers are arranged in an alternation pattern. In some implementations, the alternation pattern includes a strict alternation of gas channels and fluid channels.

According to another aspect of the disclosure, a method of manufacturing an oxygenator includes defining a first plurality of gas channels and a first plurality of fluid channels in a first polymer layer. The method also includes defining a second plurality of gas channels, a second plurality of fluid channels, and a plurality of gas vias in a second polymer layer. The method further includes defining a third plurality of gas channels and a third plurality of fluid channels in a third polymer layer. The method also includes rotating the second polymer layer with respect to the first and third polymer layers, and then aligning each of the plurality of gas vias with an inlet of each of the first plurality of gas channels and with an inlet of each of the third plurality of gas channels. The first and third polymer layers are then coupled to the second polymer layer.

In some implementations, the method also includes coupling the first polymer layer to a first surface of the second polymer layer and coupling the third polymer layer to a second surface of the second polymer layer. The first surface is opposite the second surface.

In some implementations, the second polymer layer is rotated about 180 degrees with respect to the first and third polymer layers. In some implementations, the second and third polymer layers are each a copy of the first polymer layer.

In some implementations, the method also includes aligning the first plurality of gas channels with the second plurality of fluid channels, and aligning the first plurality of fluid channels with the second plurality of gas channels.

In some implementations, the method also includes defining a second plurality of gas vias in the first polymer layer and defining a third plurality of gas vias in the third polymer layer. The method also includes forming one or more mechanical mixers in at least one of the first, second, and third plurality of fluid channels. In some implementations, the first polymer layer and the third polymer layers are coupled to the second polymer layer with a permeant adhesive, a hot-melt adhesive, plasma bonding, ultrasonic welding, friction welding, or laser welding.

According to another aspect of the disclosure, a method for oxygenating blood includes providing one of the oxygenators described herein. Oxygen is then introduced into a pressure vessel housing the oxygenator. At least partially deoxygenated blood is introduced into the oxygenator, and then at least partially oxygenated blood is received from the oxygenator.

In some implementations, the method includes pressurizing the pressure vessel with the introduced oxygen to a pressure of between about 1.0 atms and about 2.5 atms or between about 2.0 atms and about 3.0 atms. In some implementations, the method includes introducing the at least partially deoxygenated blood into the oxygenator at a rate of between about 500 mL/min and about 7 L/min.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a blood oxygenator that includes a plurality of gas and fluid channels. In some implementations, the plurality of gas and fluid channels are oxygen and blood channels arranged in a checkerboard layout. In some implementations, the checkerboard layout enables diffusion between the gas and fluid channels in four directions. For example, when viewed as a cross-section through each of the channels of the oxygenator, the checkerboard configuration includes alternating gas and fluid channels in both the x-axis (e.g., in-plane) and in the y-axis (e.g., out-of-plane) directions. The checkerboard configuration can increase diffusion efficiency compared to oxygenators that alternate between blood flow layers and oxygen flow layers because the checkerboard configuration enables diffusion in four directions (e.g., up, down, left, and right) while oxygenators with alternating blood and oxygen flow layers only enable diffusion in two directions (e.g., up and down). In some implementations, the oxygenator described herein reduces manufacturing complexity by using asymmetrical layer designs that include "open" gas channels. The inlets of the open gas channels are exposed to the ambient atmosphere. In some implementations, the oxygenator is placed within a pressure vessel to drive gas into each of the open gas channels. In some implementations, the open gas channels also reduce manufacturing complexity because a separate gas manifold is not required.

Figure 1:
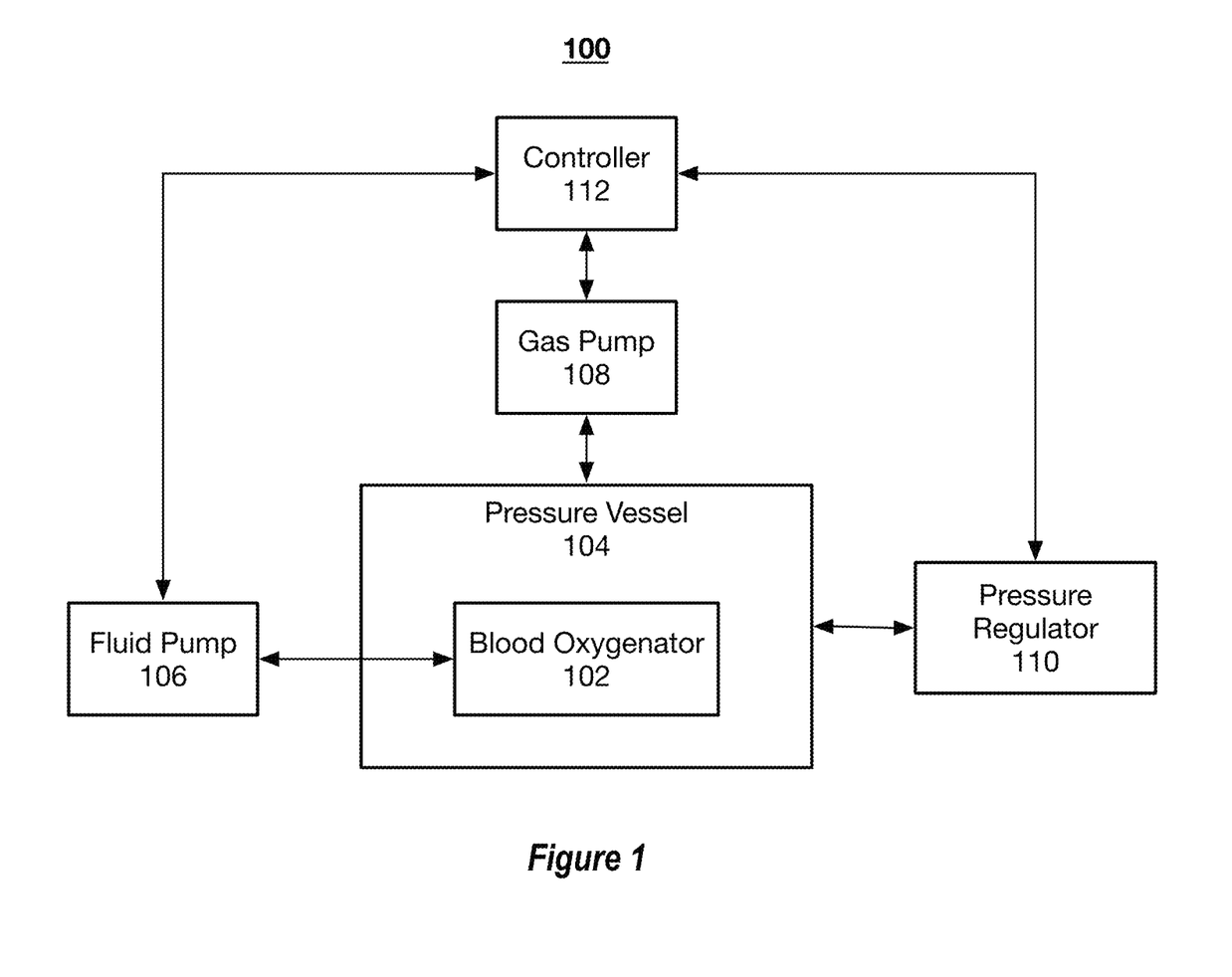
FIG. 1 illustrates an example system for oxygenating blood.

FIG. 1 illustrates an example system 100 for oxygenating blood. The system 100 includes an oxygenator 102 that is housed within a pressure vessel 104. Fluid pump 106 flows a fluid (e.g., blood) through the oxygenator 102. A gas pump 108 flow gas (e.g., oxygen) into the pressure vessel 104. One or more pressure regulators 110 regulate the pressure within the pressure vessel 104. The pumps 106 and 108 are controlled by a controller 112, which, in some implementations, receives pressure readings about the pressure vessel 104 from the pressure regulator 110.

The oxygenator 102 is described in further in relation to FIGS. 2-5B. In general, the oxygenator 102 includes a plurality of polymer substrate layers. Each of the polymer substrate layers includes a plurality of gas channels and a plurality of fluid channels. In each polymer substrate layer, the gas channels and fluid channels alternate such that each of the gas channels and each of the fluid channels (except for the channels on the edges of the polymer substrate layers) are between two fluid channels and two gas channels, respectively. The oxygenator 102 is also configured such that each of the fluid channels of a first polymer substrate layer vertically aligns with and overlaps with a gas channel of a second polymer substrate layer. Similarly, each of the gas channels of the first polymer substrate layer vertically aligns with and overlaps a fluid channel of the second polymer substrate layer. This alignment configuration is referred to as a checkerboard configuration. In the checkerboard configuration, gas channels surround (e.g., are above, blow, and on both sides) each interior fluid channel, and fluid channels surround each interior gas channel. As described further below, in some implementations, the gas channels and fluid channels alternate according to a more complex alternation pattern without departing from the scope of the disclosure.

The oxygenator 102 of the system is housed within a pressure vessel 104. To reduce the complexity of a manifold system that routes gas to each of the gas channels of the oxygenator 102, vents that supply gas to the gas channels of the oxygenator 102 are open and exposed to the ambient, atmospheric conditions created within the pressure vessel 104. In these implementations, the gas channels do not require a complex manifold for the distribution of gas (e.g., oxygen) to each of the gas channels. In these implementations, only the fluid channels of the oxygenator 102 are coupled to a manifold. The pressure vessel 104 is a pressure resistant housing that includes a hard shell configured to withstand elevated pressures. The pressure vessel 104 is manufactured from a gas impermeable plastic, such as polycarbonate, or a metal. The controller 112 controls the gas pump 108, which and pumps gas, such as oxygen, into the pressure vessel 104 to pressurize the pressure vessel 104. In some implementations, the pressure vessel 104 is pressured to between about 1 atm to about 5 atm, between about 1 atm and about 4 atm, between 1 atm and about 3 atm, or between about 1.5 atm and about 2.5 atm.

The pressure vessel 104 of the system 100 includes one or more pressure regulators 110 to regulate the pressure within the pressure vessel 104 and maintain a predetermined pressure within the pressure vessel 104. In some implementations, the pressure regulator 110 includes pressure sensors that send pressure readings to the controller 112—enabling a closed loop control of the pressure within the pressure vessel 104. In some implementations, the pressure regulator 110 is a pressure release valve that prevents build-up of pressure substantially beyond the predetermined pressure. For example, the pressure regulator 110 may by a pressure valve that automatically opens when the pressure within the pressure vessel 104 reaches 2.5 atm. Venting the pressure within the pressure vessel 104 enables the oxygen within the pressure vessel 104 to be refreshed with new oxygen. In operation, $CO_2$, diffuses out of the blood, (e.g., through, for example, the polymer layers) and into pressure vessel 104. Venting the pressure within the pressure vessel 104 also enables the $CO_2$ to escape the pressure vessel 104, such that $CO_2$ levels do not build up within the pressure vessel 104.

The system 100 also includes a fluid pump 106 that is controlled by the controller 112 and configured to flow a fluid through the oxygenator 102. For example, the fluid pump 106 is configured to flow blood through the fluid channels of the oxygenator 102. The fluid pump 106 is fluidically coupled to a manifold of the oxygenator 102 that distributes the fluid to each of the fluid channels of the oxygenator 102. The fluid pump 106 is configured to flow a fluid through the oxygenator 102 at a rate of between about 500 mL/min and about 7 L/min, between about 1.5 L/min and about 5.5 L/min, or between about 3 L/min and about 5 L/min.

Figure 2:
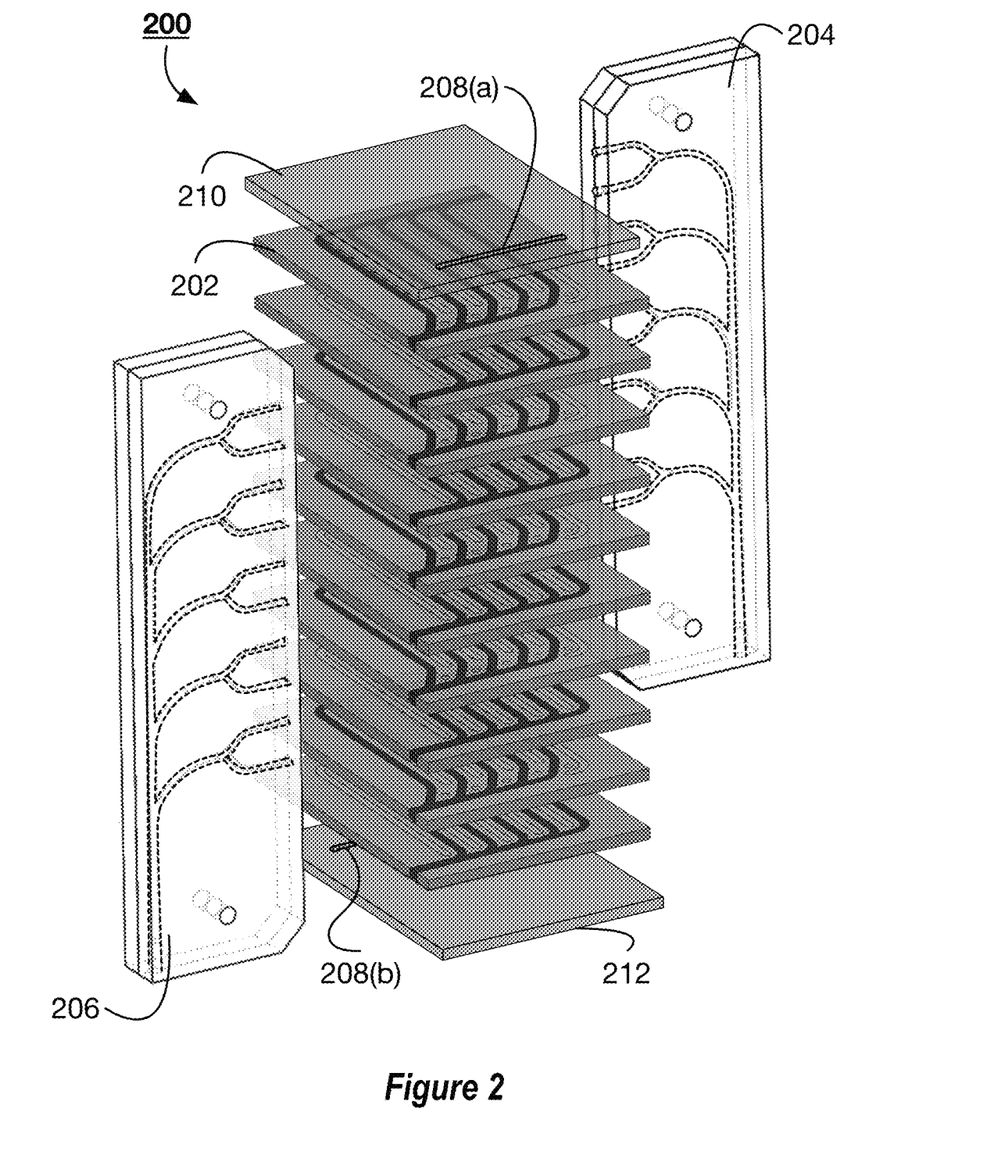
FIG. 2 illustrates an exploded view of an example oxygenator for use with the system illustrated in FIG. 1.

FIG. 2 illustrates an exploded view of an example oxygenator 200 for use with the system 100 illustrated in FIG. 1. The oxygenator 200 includes a plurality of polymer layers 202. Each of the polymer layers 202 includes a plurality of gas channels and a plurality of fluid channels. When coupled together, the polymer layers 202 create a separate fluid flow network and a separate gas flow network. In some implementations, the coupled polymer layers 202 create a fluid flow network and two separate gas flow networks. The oxygenator 200 also includes a fluid inlet manifold 204 and a fluid outlet manifold 206. Fluid, such as blood, flows to each of the fluid channels of the different polymer layers through the fluid inlet manifold 204 and the fluid outlet manifold 206 collects the fluid as the fluid exits each of the polymer layers 202. The oxygenator 200 includes vents 208(a) and 208(b) within the top layer 210 and bottom layer 212, respectively. The top layer 210 and bottom layer 212 do not include gas and fluid channels, and the vents 208 provide the inlets to the gas channels in the top most and bottom most polymer layers. The vents provide the inlets to the gas channels access to the ambient environment within the pressure vessel housing the oxygenator 200. The vent 208(a) provide access to the gas channels of a first gas flow network and the vent 208(b) provide access to the gas channels of a second gas flow network.

The inlet manifold 204 and the outlet manifold 206 are configured to introduce and receive blood from each of the polymer layers 202 without causing substantial damage to the blood. For example, both the inlet manifold 204 and the outlet manifold 206 include gradual curving channels rather than right angles. In some implementations, the channels within the manifold mimic vascular channels. For example, the channels split at bifurcations. After a bifurcation the size of the channel is reduced according to Murray's Law.

Each of the polymer layers 202 of oxygenator 200 are stacked upon one another such that the channels in a first polymer layer 202 substantially overlap and run parallel with the channels of polymer layers 202 on either side of the first polymer layer 202. In some implementations, the oxygenator 200 includes between 10 and 100, between 30 and 80, or between 40 and 60 stacked polymer layers 202. In some implementations, the polymer layers 202 are manufactured from Poly(DiMethylSiloxane) (PDMS) and are directly stacked upon one another. For example, when the channels of the polymer layers 202 are defined within a PDMS layer, oxygen can saturate from the gas channels and into the PDMS. The PDMS then serves as a source of oxygen for the fluid channels aligned horizontally and vertically with the gas channel. In other implementations, the polymer layers 202 are manufactured from thermoplastics, such as polystyrene, polycarbonate, polyimide, or cyclic olefin copolymer (COC), biodegradable polyesters, such as polycaprolactone (PCL), or soft elastomers such as polyglycerol sebacate (PGS). In these implementations, each of the polymer layers 202 are separated from one another by a semi-porous membrane selected to permit diffusion of oxygen or other gas between the fluid channels and the gas channels.

In some implementations, the polymer layers 202 include an alternating channel pattern of gas channel and fluid channels. For example, the alternation pattern can include a strictly alternating pattern where each fluid channel is between two gas channels and each gas channel is between two fluid channels (other than at the edges of the polymer layers 202). In other implementations, the alternation pattern may include multiple gas channels or multiple fluid channels next to one another. For example, the polymer layer 202 could include an alternation pattern that includes two gas channels, then two fluid channels, then two gas channels, then two fluid channels, and so forth. In some other implementations, the alternation pattern may include multiple fluid channels alternating with one gas channel having a width about equal to the sum of widths of the multiple fluid channels and the widths of the walls separating the respective fluid channels, followed by another set of fluid channels. When stacked, each gas channel in a given polymer layer 202 would be positioned substantially in alignment with, and under or over, a corresponding set of multiple fluid channels. While a variety of alternation patterns can be suitable for the system described herein, the remaining portion of the disclosure assumes a strictly alternation pattern; however, one of ordinary skill in the art would appreciate the systems described herein may be implemented within any alternation pattern.

Figure 3A:
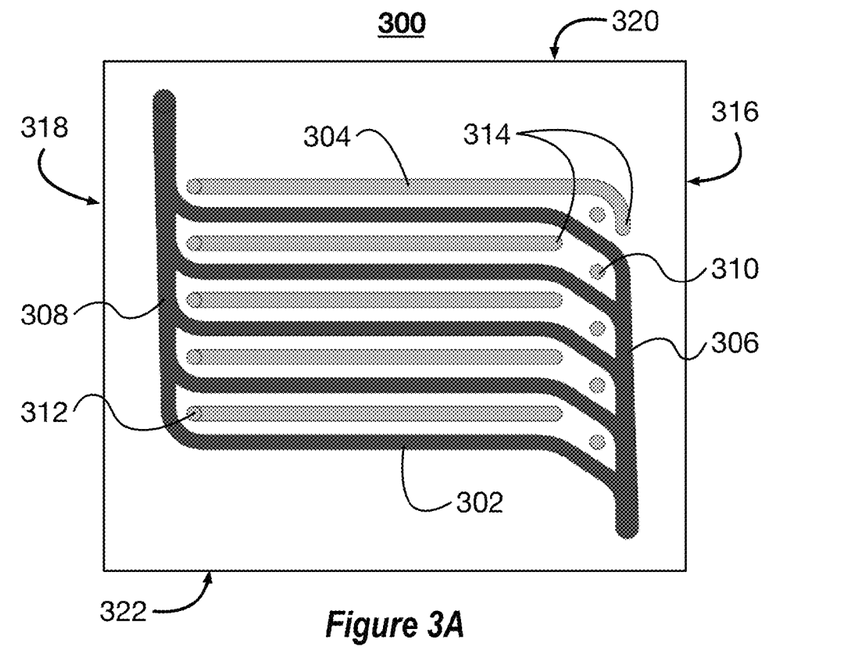
FIGS. 3A and 3B illustrate top views of an example polymer layer for use in the oxygenator illustrated in FIG. 1.
Figure 3B:
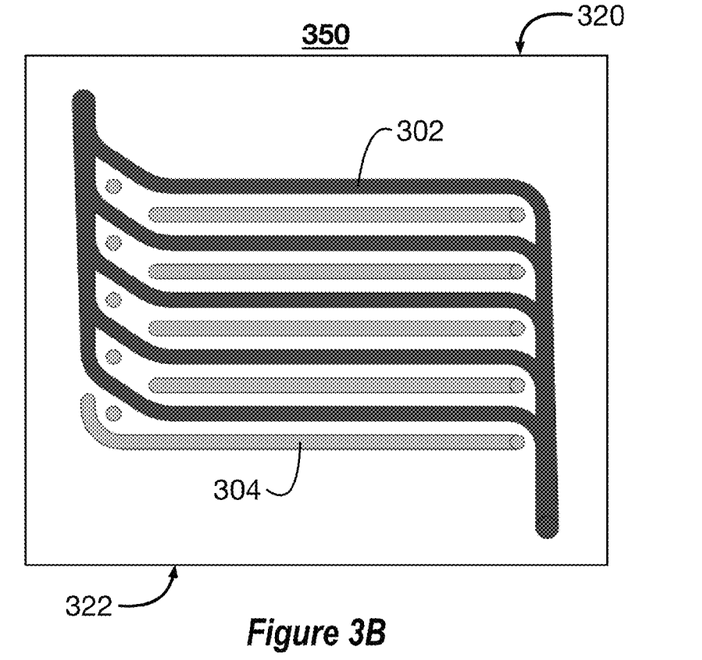

FIGS. 3A and 3B illustrate top views of an example polymer layer 300 for use in the oxygenator 102 of FIG. 1. Each polymer layer 300 defines a plurality of fluid channels 302 and a plurality of gas channels 304. A primary input channel 306 is fluidically coupled to each of the plurality of fluid channels 302. The primary input channel 306 provides fluid to each of the fluid channels 302 a fluid inlet of the oxygenator, such as the fluid inlet 204 described in relation to FIG. 2. Similarly, a primary outlet channel 308 collects the fluid exiting each of the fluid channels 302. The primary outlet channel provides the fluid to the fluid outlet of the oxygenator, such as the fluid outlet 206 described in relation to FIG. 2. The polymer layer 300 also includes a plurality of gas vias 310. The gas vias couple the gas channels in a polymer layer above the polymer layer 300 to the gas channels in a polymer layer below the polymer layer 300. In this example, the gas channels of the polymer layer 300 are in a first gas flow network and the gas channels in the polymer layers above and below the polymer layer 300 are in a second gas flow network. Each of the gas vias 310 is aligned with one of the fluid channels 302. The gas vias 310 are aligned with the fluid channels 302 to enable the gas vias 310 to provide gas to the gas channels 302 that overlap the fluid channels 302 in adjacent polymer layers.

As illustrated, each of the fluid channels 302 are supplied by a primary inlet 306 within the same polymer layer 300 as the fluid channels 302. Also, the fluid exits the fluid channels 302 to a primary outlet channel 308 that is also within the same polymer layer 300 as the fluid channels 302. In contrast, each of the gas channels 304 includes a gas inlet 312, which receives gas from a gas via 310 formed in a polymer layer above or below the polymer layer 300. The end 314 of the gas channels 304 opposite the gas inlets 312 are dead ends and do not exit to another channel or layer. In some implementations, the dead ends increase the pressure within the gas channels 304 and forces the gas flowing into the gas channels 304 into the polymer layer 300 and/or a membrane separating the polymer layer 300 from other polymer layers.

In some implementations, the fluid channels 302 are configured to distribute blood while protecting blood health. For example, the walls of the fluid channels 302 can be coated with an anticoagulant to prevent clotting of blood as the blood flows through the fluid channels 302. Also to protect the health of the blood flowing through the fluid channels 302, the fluid channels 302 can include gradual angles rather than right angles. For example, the primary input channel 306 gradually transitions into the fluid channels 302 and the fluid channels 302 gradually transition into the primary outlet channel 308.

In some implementations, the relative dimensions of channels are selected to follow Murray's Law. In some implementations, the fluid channels 302 are between about 1 cm and about 40 cm, between about 10 cm and about 30 cm, or between about 15 cm and about 25 cm long. The fluid channels 302 are between about 100 µm and about 1000 µm, between about 300 µm and about 800 µm, or between about 500 µm and about 600 µm wide (across the majority of their lengths). The fluid channels 302 are between about 40 µm and about 250 µm, between about 100 µm and about 200 µm, or between about 100 µm and about 150 µm deep. As illustrated the polymer layer 300 includes five fluid channels 302 and five gas channels 304. In some implementations, each polymer layer 300 includes between about 5 and about 100, between about 20 and about 80, or between about 40 and about 60 fluid channels 302. In some implementations, each polymer layer 300 includes between about 5 and about 100, between about 20 and about 80, or between about 40 and about 60 gas channels 304.

In some implementations, the fluid channels 302 include mechanical features that stimulate mixing of the blood as it flows through the channels. For example, one or more walls of the fluid channels 302 can include pits, posts, ridges, grooves, or a combination thereof that mix the floods as it flows through the fluid channels 302.

In some implementations, the polymer layers 300 have an asymmetrical design. The polymer layer 300 is asymmetrical because the polymer layer 300 does not include a line of symmetry. For example, the right side 316 of the polymer layer 300 includes the gas vias 310 while the left side 318 of the polymer layer 300 does not include the gas vias 310. The polymer layer 300 is also asymmetrical front to back. For example, the front most channel on the front side 320 of the polymer layer 300 is a gas channel 304 and the backmost channel on the backside 322 of the polymer layer 300 is a blood channel 302. The asymmetrical configuration reduces the complexity of manufacturing because the same polymer layer design can be copied multiple times and then, during the stacking process, alternating polymer layers can be rotated 180 degrees to create a checkerboard configuration. The asymmetrical configuration enable the checkerboard configuration without the need for manufacturing different types of polymer layers or for manufacturing symmetrical polymer layers that are then offset when stacked to produce a checkerboard configuration. The shifting of the symmetrical polymer layers can require a complex manifold system to provide fluid and gas to each of the fluid and gas channels.

In some implementations, each of the gas vias 310 is inline with one of the fluid channels 302 such that the gas via 310 can supply gas to a gas channel 304 that is above and below the fluid channel 302 in the polymer layer 300. When inline with one of the fluid channels 302, the gas via 310 is aligned with a longitudinal axis of the fluid channel 302. In some implementations, the diameter of the gas vias 310 is the same as the width of the gas channels 304. In some implementations, the gas vias 310 have a diameter that is larger than the width of the gas channels 304. In some implementations, each gas channel 304 may be connected to multiple gas vias 310. The gas vias 310 are spaced and sized to enable the fluid channels 302 to branch from the primary inlet 306 and pass between the gas vias 310.

FIG. 3B illustrates the polymer layer 350. The polymer layer 350 is configured the same as the polymer layer 300 illustrated in FIG. 3A, except the polymer layer 350 is rotated 180 degrees. When rotated, the front most channel on the front side 320 of the polymer layer 300 is now a fluid channel 302 and the backmost channel on the backside 322 of the polymer layer 300 is now a gas channel 304. If polymer layers 300 and 350 were stacked, a gas channel 304 would overlap each of the fluid channels 302 and a fluid channel 302 would overlap each of gas channels 304.

Figure 4:
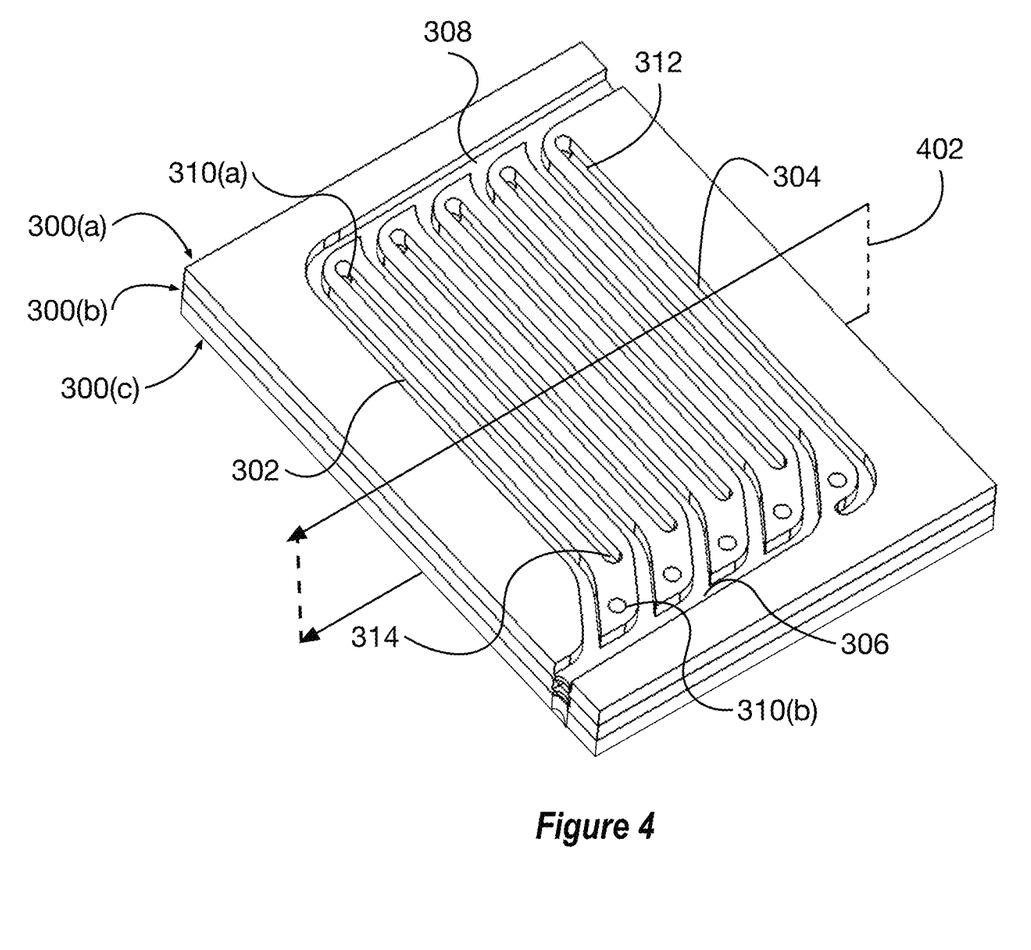
FIG. 4 illustrates three polymer layers stacked upon each other.

FIG. 4 illustrates three polymer layers 300 (polymer layer 300(a), 300(b), and 300(c)) stacked upon each other. Polymer layer 300(b) is rotated 180 degrees with respect to polymer layers 300(a) and 300(c) to create the checkerboard configuration with alternating gas and fluid channels both in-plane (within a layer) and out-of-plane (along the stacked layers). FIG. 4 illustrates that the gas channels 304 in every other layer are connected through gas vias 310. For example, the gas via 310(a), which is defined in polymer layer 300(b), connects a gas channel 304 in the polymer layer 300(a) with a gas channel 304 in the a polymer layer 300(c). The gas channels 304 of the polymer layer 300(a) and 300(b) define a first gas flow network. The gas via 310(b) supplies gas to a gas channel 302 in the polymer layer 300(b). The gas channels 304 in the polymer layer 300(b) define a second gas network. The first and second gas networks are not in direct communication with one another.

Figure 5A:
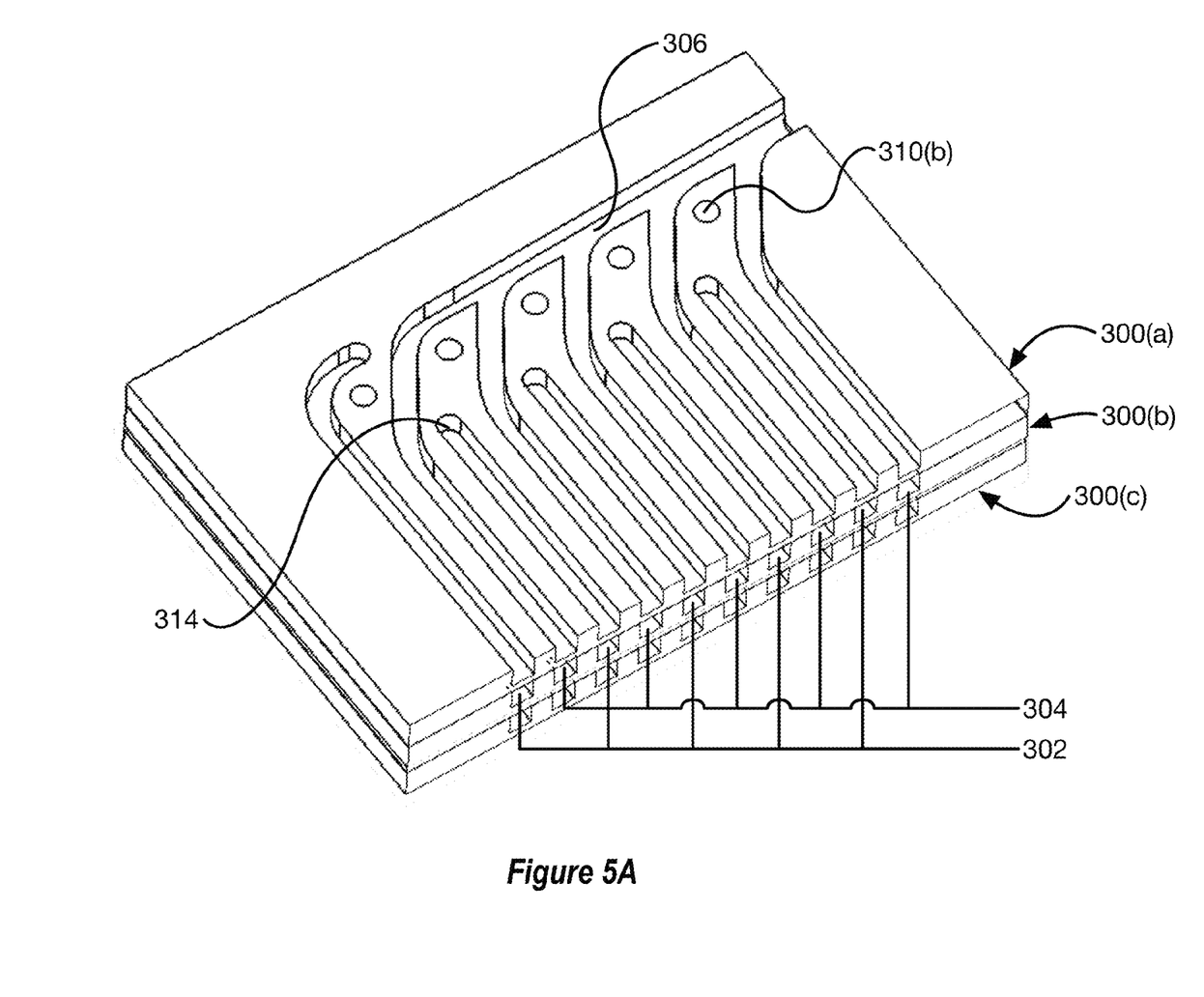
FIG. 5A illustrate a cutaway view made along a cut plane of the three polymer layer stack illustrated in FIG. 4.

FIG. 5A illustrate a cutaway view made along the cut plane 402 of the three-polymer stack illustrated in FIG. 4. The cutaway view illustrates the above described checkerboard design of alternating gas and fluid channels both in-plane and out-of-plane. The checkerboard design is further illustrated in FIG. 5B. The gas channels 304 of the polymer layer 300(a) dead end at dead ends 314 and are not coupled to the gas vias 310 that supply gas to the gas channels 304 of the polymer layer 300(b).

Figure 5B:
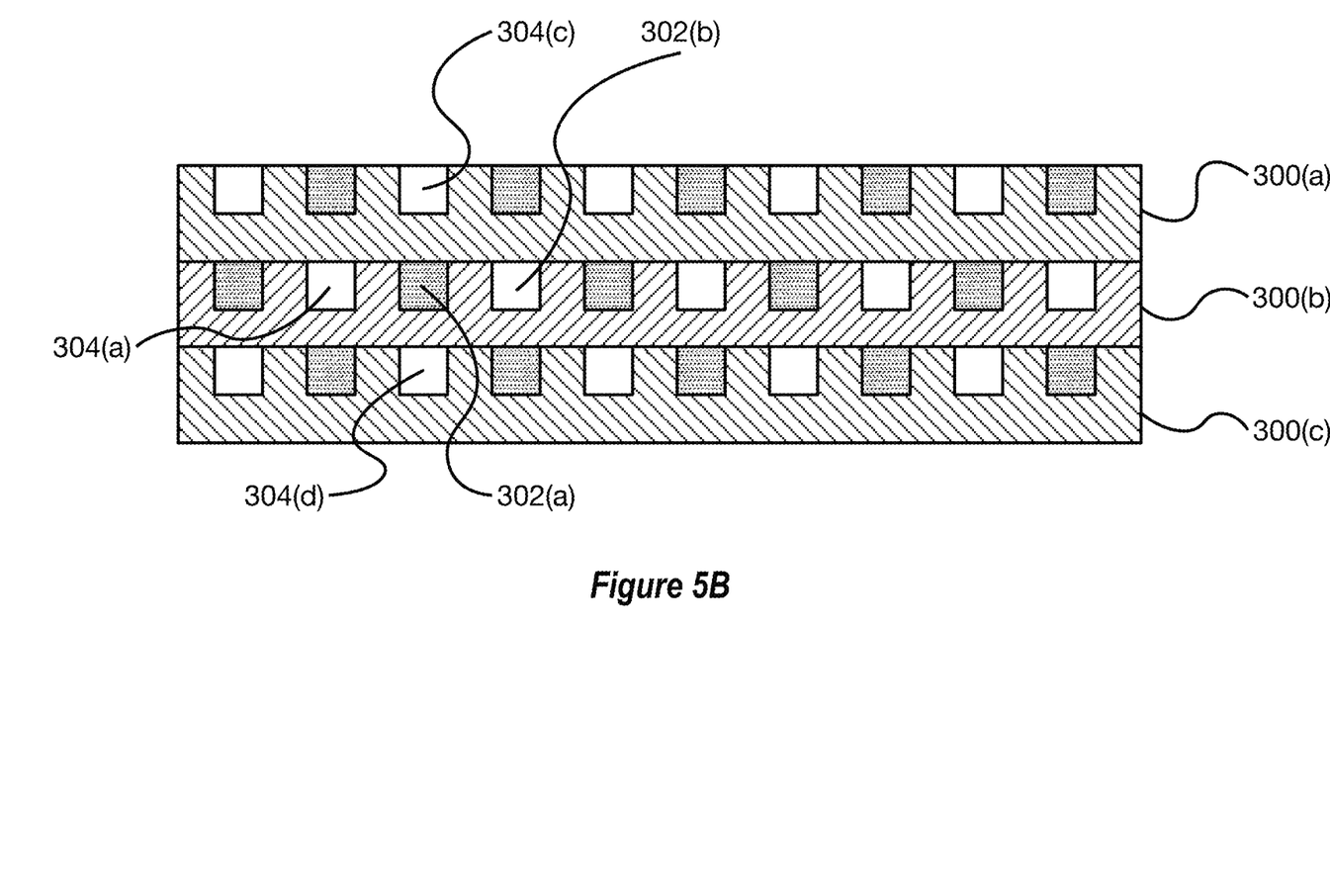
FIG. 5B illustrates a schematic of the cross-section view made along the cut plane of the three-polymer stack illustrated in FIG. 4.

FIG. 5B illustrates a schematic of the cross-sectional view made along the cut plane 402 of the three-polymer stack illustrated in FIG. 4. As described above, the channels are arranged in a checkerboard design. For example, fluid channel 302(a) is surround in-plane by gas channels 304(a) and 304(b) and out-of-plane by gas channels 304(c) and 304(d). The gas from each of the gas channels 304(a)-304(d)

diffuses into their respective polymer layers and provides a gas source along each of the four walls of the fluid channel 302(a).

In some implementations, having the polymer layer act as a gas source reduces the alignment tolerance needed to construct the oxygenator. For example, as oxygen passes through the gas channels the oxygen can saturate the polymer layers and act as a gas source to the fluid channels even if the gas channel is not perfectly aligned with the fluid channel. In devices where a membrane separates two non-gas permeable channel containing layers, diffusion substantially only occurs through the membrane at locations where gas and fluid channels overlap. In some implementations of the oxygenators described herein, because a substantial portion of the polymer layer acts as a gas source to the fluid channels rather than just the portion of the membrane at overlapping areas of gas and fluid channels, the alignment and overlap tolerances of the gas and fluid channels can be lower in the devices described herein than compared to membrane based devices. Therefore, in some implementations, the gas channels and the fluid channels in different polymer layers of the devices described herein can be at least partially offset from one another without departing from the scope of the invention.

As illustrated, each of the gas channels 304 and the fluid channels 302 are defined as troughs in a surface of the polymer layer. The trough defines the sidewalls and the floor of the gas channels 304 and fluid channels 302. The ceiling of each of the channels is provided by a bottom surface of a polymer layer that is stacked upon the surface of the polymer layer 300 that defines the troughs. For example, if the channels of the oxygenator illustrated in FIG. 5B were manufactured as troughs through each of the polymer layers 300, the bottom surface of the polymer layer 300(a) would provide the ceiling to the troughs defined in polymer layer 300(b). In some implementations, a top layer that does not include any channels provides the ceiling for the channels defined in the polymer layer 300(a).

In some implementations, the thickness of the walls separating adjacent channels is selected to control the diffusion between the gas channels 304 and the fluid channels 302. In some implementations, the thickness of the walls separating adjacent channels is between about 1 µm and about 100 µm, between about 10 µm and about 100 µm, or between about 10 µm and about 25 µm thick. In some implementations, the thickness of the floor (or ceiling) separating channels in adjacent polymer layers is between about 1 µm and about 100 µm, between about 10 µm and about 100 µm, or between about 10 µm and about 25 µm thick. In some implementations, the total thickness of each of the polymer layers is between about 45 µm and about 350 µm, between about 100 µm and about 300 µm, between about 150 µm and about 250 µm, or between about 150 µm and about 200 µm. In general, the gas channels 304 and the fluid channels 302 are formed in materials having a relatively high permeability to oxygen, for example PDMS. In some implementations, the polymer layers are manufactured from polymers with an oxygen gas permeance greater than about $1\times10^{-6}$ mL/s/cm$^2$/cm Hg, about $1\times10^{-5}$ mL/s/cm$^2$/cm Hg, about $3\times10^{-5}$ mL/s/cm$^2$/cm Hg, about $7\times10^{-5}$ mL/s/cm$^2$/cm Hg, or greater than about $1\times10^{-4}$ mL/s/cm$^2$/cm Hg.

In some implementations, manufacturing the polymer layers 300 from materials with relatively high permeability to oxygen enables the polymer layers 300 to be directly stacked on one another without the need of a gas permeable membrane between the polymer layers 300. In some implementations, the gas channels 304 and the fluid channels 302 are separated from one another (in-plane and out-of-plane) by between about 25 µm and about 200 µm, between about 25 µm and about 150 µm, between about 25 µm and about 100 µm, or between about 25 µm and about 75 µm.

Figure 6:
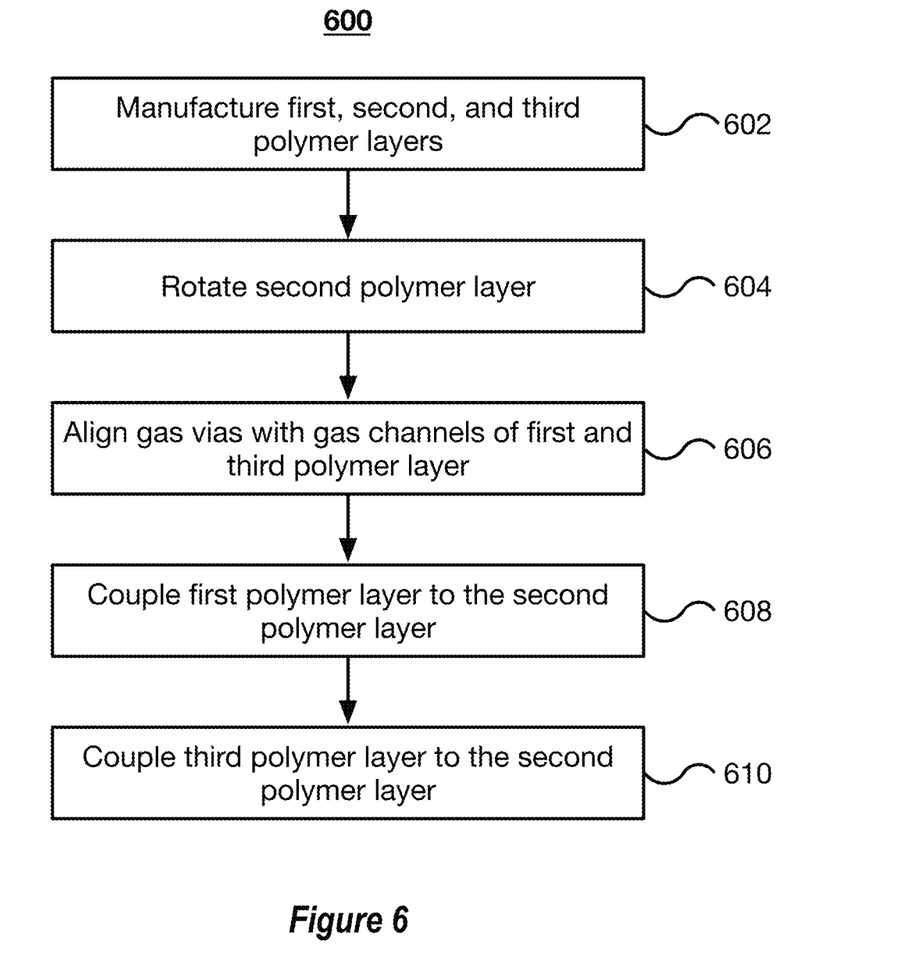
FIG. 6 illustrates a flow chart of an example method for manufacturing a blood oxygenator of the system illustrated in FIG. 1.

FIG. 6 illustrates a flow chart of an example method 600 for manufacturing a blood oxygenator. The method 600 includes manufacturing first, second, and third polymer layers (step 602). The second polymer layer is rotated with respect to the first and second polymer layers (step 604). The gas vias of the second polymer layer is aligned with the gas inlets of the first and third polymer layers (step 606). The first polymer layer is coupled to second polymer layer (step 608), and the third polymer layer is coupled to the second polymer layer (step 610).

As set forth above, the method 600 includes manufacturing first, second, and third polymer layers (step 602). Each of the first, second, and third polymer layers include a plurality of gas channels and a plurality of fluid channels. Each of the polymer layers also include a gas via that connects the gas channels in the polymer layers above and below the polymer layer together without connecting to the gas channels within the given polymer layer. In some implementations, as illustrated in FIG. 3A, each of the gas channels of a polymer layer include inlets 312 that couple to the gas vias of neighboring polymer layers. The end of the gas channel opposite the inlet 312 is a dead end 314. The gas and fluid channels of each of polymer layers can be defined in each of the polymer layers by etching, milling, stamping, stamping, direct micromachining, injection molding, or a combination thereof.

The method 600 also includes rotating the second polymer layer (step 604). As described above, each of the polymer layers are asymmetric such that polymer layer does not have a line of symmetry. The asymmetrical configuration of the polymer layer enables each of the first, second, and third polymer layers to be copies of one another. Rotating the second polymer layer 180 degrees enables the oxygenator to have the above described checkerboard design.

The method 600 also includes aligning the gas vias of the second polymer layer with the gas inlets of the first and third polymer layers (step 606). As described above in relation to FIG. 3A, one side of each of the polymer layers includes gas inlets 312 and the other side of the polymer layer includes gas vias 310. When the second polymer layer is rotated, the gas vias 310 of the second layer can be aligned with the gas inlets 312 of the first and the second polymer layers. Also, the gas channels of the second polymer layer are aligned with the fluid channels of the first and third polymer layers and the fluid channels of the second polymer layer are aligned with the gas channels of the first and third polymer layers.

The method also includes coupling the first polymer layer to the second polymer layer (step 608) and coupling the third polymer layer to the second polymer layer (step 610). The first polymer layer is coupled to a first surface of the second polymer layer and the third polymer layer is coupled to a second surface of the second polymer layer. The second surface is opposite the second surface of the second polymer layer such that the second polymer layer is sandwiched between the first and third polymer layers. In some implementations, the layers of the oxygenator are reversibly coupled together by, for example, clamping the layers together. In other implementations, the layers are permanently coupled together with permeant adhesives (e.g., RTV), hot-melt adhesives (e.g., 3M Scotch-Weld 3738 and 3762), plasma bonding, ultrasonic welding, friction welding, or laser welding. In some implementations, the additional polymer layers are coupled to the three-polymer layer stack.

In some implementations, the method 600 includes manufacturing additional polymer layers. In these implementations, ever other polymer layer is rotated prior to coupling the polymer layer to the stacked polymer layers. In some implementations, the oxygenator includes between 5 and 100 polymer layers.

The disclosed system and methods may be embodied in other specific forms without departing from the spirit or essential characteristics thereof. The forgoing implementations are therefore to be considered in all respects illustrative, rather than limiting of the invention.

What is claimed:

1. An oxygenator comprising:
   a first polymer layer comprising a first plurality of gas channels and a first plurality of fluid channels;
   a second polymer layer comprising a second plurality of gas channels and a second plurality of fluid channels, each of the second plurality of gas channels overlapping one of the first plurality of fluid channels and each of the second plurality of fluid channels overlapping one of the first plurality of gas channels;
   a third polymer layer comprising a third plurality of gas channels and a third plurality of fluid channels, each of the third plurality of gas channels overlapping one of the second plurality of fluid channels and each of the third plurality of fluid channels overlapping one of the second plurality of gas channels; and
   a plurality of gas vias defined in the second polymer layer, each of the plurality of gas vias coupling one of the first plurality of gas channels to one of the third plurality of gas channels.

2. The oxygenator of claim 1, further comprising a second plurality of gas vias defined in the first polymer layer and a third plurality of gas vias defined in the third polymer layer.

3. The oxygenator of claim 1, wherein the first plurality of gas channels and the third plurality of gas channels define a first gas flow network and the second plurality of gas channels defines a second gas flow network.

4. The oxygenator of claim 1, wherein each of the second plurality of fluid channels are substantially vertically aligned with one of the first plurality of gas channels, each of the third plurality of gas channels are substantially vertically aligned with one of the second plurality of fluid channels, and each of the third plurality of fluid channels are substantially vertically aligned with one of the second plurality of gas channels.

5. The oxygenator of claim 1, wherein the first plurality of gas channels and the first plurality of fluid channels are arranged in an alternation pattern, the second plurality of gas channels and the second plurality of fluid channels are arranged in the alternation pattern, and the third plurality of gas channels and the third plurality of fluid channels are arranged in the alternation pattern.

6. The oxygenator of claim 5, wherein the alternation pattern comprises a strict alternation of gas channels and fluid channels.

7. The oxygenator of claim 1, further comprising a pressure vessel housing the first, second, and third polymer layers.

8. The oxygenator of claim 7, wherein an inlet to the first, second, and third plurality of gas channels is open to an ambient environment within the pressure vessel.

9. The oxygenator of claim 1, wherein the first plurality of gas channels and the first plurality of fluid channels are configured in an asymmetrical channel layout, and the second plurality of gas channels and the second plurality of fluid channels are configured in the asymmetrical channel layout.

10. The oxygenator of claim 1, wherein the second and third polymer layers are each a copy of the first polymer layer.

11. The oxygenator of claim 10, wherein the second polymer layer is rotated 180 degrees with respect to the first and third polymer layers.

12. The oxygenator of claim 1, wherein each of the channels of the first, second, and third plurality of gas channels comprise a dead end.

13. The oxygenator of claim 1, wherein each of the plurality of gas vias is positioned between two of the plurality of fluid channels of the second polymer layer.

14. The oxygenator of claim 1, wherein each of the plurality of gas vias is aligned with a longitudinal axis of one of the plurality of fluid channels in the second polymer layer.

15. The oxygenator of claim 1, wherein a depth of the first, second, and third plurality of fluid channels is between about 40 μm and about 250 μm.

16. The oxygenator of claim 1, wherein the first, second, and third polymer layers each comprise Poly(DiMethylSiloxane).

17. The oxygenator of claim 1, wherein the first, second, and third polymer layers each have a gas permeance greater than about $1 \times 10^{-6}$ mL/s/cm$^2$/cm Hg.

18. A method of oxygenating blood, the method comprising:
    providing an oxygenator according to claim 1;
    introducing oxygen into pressure vessel housing the oxygenator;
    introducing at least partially deoxygenated blood into the oxygenator; and
    receiving at least partially oxygenated blood from the oxygenator.

19. The method of claim 18, further comprising pressurizing the pressure vessel with the introduced oxygen to a pressure of between about 1.0 atms and about 2.5 atms.

20. The method of claim 18, further comprising pressurizing the pressure vessel with the introduced oxygen to a pressure of between about 2.0 atms and about 3.0 atms.

21. The method of claim 18, further comprising introducing the at least partially deoxygenated blood into the oxygenator at a rate of between about 500 mL/min and about 7 L/min.

* * * * *